(12) United States Patent
Barda-Saad

(10) Patent No.: US 11,266,601 B2
(45) Date of Patent: Mar. 8, 2022

(54) LIPOSOMES FOR MODULATING WISKOTT-ALDRICH SYNDROME PROTEIN

(71) Applicant: BAR-ILAN UNIVERSITY, Ramat Gan (IL)

(72) Inventor: Mira Barda-Saad, Gannei Tikva (IL)

(73) Assignee: BAR ILAN UNIVERSITY, Ramat Gan (IL)

( * ) Notice: Subject to any disclaimer, the term of this patent is extended or adjusted under 35 U.S.C. 154(b) by 0 days.

(21) Appl. No.: 16/933,505

(22) Filed: Jul. 20, 2020

(65) Prior Publication Data

US 2020/0345640 A1 Nov. 5, 2020

Related U.S. Application Data

(62) Division of application No. 16/173,899, filed on Oct. 29, 2018, now Pat. No. 10,765,631, which is a division of application No. 14/895,734, filed as application No. PCT/IB2014/061907 on Jun. 3, 2014, now Pat. No. 10,154,962.

(60) Provisional application No. 61/830,178, filed on Jun. 3, 2013.

(51) Int. Cl.

| | |
|---|---|
| *C07H 21/02* | (2006.01) |
| *C07H 21/04* | (2006.01) |
| *A61K 9/127* | (2006.01) |
| *C12N 15/11* | (2006.01) |
| *C12N 15/113* | (2010.01) |
| *A61K 47/68* | (2017.01) |
| *A61K 31/415* | (2006.01) |
| *A61K 31/4155* | (2006.01) |
| *A61K 31/4192* | (2006.01) |
| *A61K 31/435* | (2006.01) |
| *A61K 31/437* | (2006.01) |
| *A61K 31/4402* | (2006.01) |
| *A61K 31/445* | (2006.01) |
| *A61K 31/4545* | (2006.01) |
| *A61K 31/496* | (2006.01) |
| *A61K 31/5377* | (2006.01) |
| *A61K 38/00* | (2006.01) |
| *C12N 15/88* | (2006.01) |

(52) U.S. Cl.
CPC ............ *A61K 9/127* (2013.01); *A61K 31/415* (2013.01); *A61K 31/4155* (2013.01); *A61K 31/4192* (2013.01); *A61K 31/435* (2013.01); *A61K 31/437* (2013.01); *A61K 31/4402* (2013.01); *A61K 31/445* (2013.01); *A61K 31/4545* (2013.01); *A61K 31/496* (2013.01); *A61K 31/5377* (2013.01); *A61K 47/6803* (2017.08); *A61K 47/6849* (2017.08); *A61K 47/6889* (2017.08); *C12N 15/111* (2013.01); *C12N 15/113* (2013.01); *A61K 38/00* (2013.01); *C12N 15/88* (2013.01); *C12N 2310/14* (2013.01); *C12N 2320/32* (2013.01)

(58) Field of Classification Search
CPC .......................... C12N 2310/14; C12N 15/113
See application file for complete search history.

(56) References Cited

U.S. PATENT DOCUMENTS

| | | | |
|---|---|---|---|
| 2006/0172003 | A1 | 8/2006 | Meers et al. |
| 2008/0113351 | A1 | 5/2008 | Naito |
| 2011/0177155 | A1 | 7/2011 | Peer |
| 2012/0077734 | A1 | 3/2012 | Cox |
| 2014/0341975 | A1 | 11/2014 | Livneh |

FOREIGN PATENT DOCUMENTS

| | | |
|---|---|---|
| JP | 2003-514843 | 4/2003 |
| JP | 2007-169269 | 7/2007 |
| JP | 2014-527533 | 10/2014 |
| WO | 99/32628 A2 | 7/1999 |
| WO | 2004/045543 A3 | 6/2004 |
| WO | 2007/127219 A2 | 11/2007 |
| WO | 2011/107772 A1 | 9/2011 |
| WO | 2013/030831 | 3/2013 |

OTHER PUBLICATIONS

Wang et al. (Biomaterials, 33, 20, 2012, 5107-5114).*
Burianek et al. (Seminars in Cell & Developmental Biology, 24, 2013, 258-266).*
Bidwell et al. (Expert Opin. Drug Deliv.,2009, 6(10), 1033-1047).*
Reicher B. et al. "WASp and WAVE Proteins: From Structure, Through Function, to Clinical Aspects" Clinical & Cellular Immunology, S12, Sep. 5, 2012, available at http://dx.doi.org/10.4172/2155-9899.S12-001.
Reicher B. et al. "Ubiquitylation-Dependant Negative Regulation of WASp is Essential for Actin Cytoskeleton Dynamics" Molecular and Cellular Biology 32(15):3153-3163, Mar. 19, 2012.
Manjunath, N., and Derek M. Dykxhoom. "Advances in synthetic siRNA Delivery". Discovery Medicine, 9(48):418-430, May 7, 2010.
Massaad MJ et al. "A WIP peptide restores WASP levels and actin cytoskeleton reorganization in lymphocytes from patients with WAS mutations that disrupt WIP binding" J. Allergy Clin Immunol 127 (4): 998-1005.e2 Apr. 2011.
Stephens et al. 1995, "KIM127, an Antibody that Promotes Adhesion, Maps to a Region of CD18 that Includes Cysteine-Rich Repeats," Cell Communication & Adhesion 3(5):375-84. (1995).

(Continued)

*Primary Examiner* — Amy H Bowman
(74) *Attorney, Agent, or Firm* — Browdy and Neimark, PLLC

(57) ABSTRACT

Embodiments of the invention relate to liposomes comprising: a lipid bilayer having an internal cavity; a therapeutic agent within the internal cavity configured to modify expression or degradation of WASp in a cell; and a targeting moiety external to the lipid bilayer configured to target an extracellular domain of a cell. Embodiments of the invention relate to methods of treatment of disease comprising administering the liposomes. Novel pharmaceutical compositions are also disclosed.

16 Claims, 2 Drawing Sheets

Specification includes a Sequence Listing.

(56) References Cited

OTHER PUBLICATIONS

Lu et al. "Epitope Mapping of Antibodies to the C-Terminal Region of the Integrin Beta2 Subunit Reveals Regions that become Exposed Upon Receptor Activation," J Immunol. May 1, 2001; 166(9):5629-37.

Wu, et al., Tyrosine Phosphorylation Regulates the SH3-mediated Binding of the Wiskott-Aldrich Syndrome Protein to PSTPIP, a Cytoskeletal-associated Protein, J Biol Chem, , vol. 273, No. 10. pp. 5765-5770 (1998).

STIC search results (STIC Accession No. 545136), Jun. 13, 2017, pp. 1-46.

\* cited by examiner

LIPOSOMES FOR MODULATING WISKOTT-ALDRICH SYNDROME PROTEIN

The Sequence Listing in ASCII text file format of 4,691 bytes in size, created on Jul. 20, 2020, with the file name "2020-07-20Sequence_Listing-BARDA-SAAD1B," filed in the U.S. Patent and Trademark Office on even date herewith, is hereby incorporated herein by reference.

TECHNICAL FIELD

Embodiments of the invention relate to liposomes and methods for treating disease using them.

BACKGROUND

Wiskott-Aldrich syndrome protein (WASp) is a protein expressed in hematopoietic cells, the cells responsible for formation of blood components. WASp-family proteins are cytoskeletal proteins which are involved in actin polymerization, a process which is responsible for cell proliferation, motility, invasion and metastasis. WASp is a founding member of the Wiskott-Aldrich syndrome (WAS) family of proteins that share similar domain structure, and are involved in actin polymerization.

In addition to WASp, a human protein known as WASp interacting protein (WIP) is also expressed in hematopoietic cells. WIP binds to WASp and is involved in actin polymerization. Mutations or deletions in the Wiskott-Aldrich syndrome gene leading to lower levels of expression of properly functional WASp protein may lead to Wiskott-Aldrich syndrome (WAS). WAS is a rare hereditary disease, mainly prevalent in males, in which patients may suffer from a compromised immune system, eczema, autoimmunity and malignancies.

Another, less severe genetic disorder related to WASp and presenting similar symptoms to WAS is X-linked thrombocytopenia (XLT) characterized by low platelet counts, diarrhea and uncontrollable bleeding. Currently, treatments for WAS and XLT are focused on treating symptoms of the diseases rather than modifying WASp expression and function.

SUMMARY

The inventors have found that WASp and WIP are overexpressed in hematopoietic malignancies associated with mutated hematopoietic cells. Hematopoietic cells, in particular lymphocytes, in which an overexpression of WASp was detected, showed increased cellular migration, cellular invasiveness and extra-cellular matrix (ECM) degradation compared to normal lymphocytes in which WASp was not overexpressed.

In malignancies associated with hematopoietic cells, such as Precursor B or Precursor T Acute Lymphocytic Leukemia (ALL), Non-Hodgkin's Lymphoma (NHL) and Chronic lymphocytic Leukemia (CLL), malignant cells tend to form membrane structures such as invadopodia for cell invasion, cell migration and cellular proliferation, thereby enabling the malignancy to spread and metastasize in various organs. Metastases associated with hematopoietic malignancies are indicative of a poor prognosis, potentially leading to a lethal outcome of the disease.

In an aspect of an embodiment of the invention, there is provided a method of targeting lymphocytes overexpressing WASp in patients suffering from malignancies associated with hematopoietic cells. Lymphocytes overexpressing WASp may be targeted by administering to a patient in need thereof a liposome that targets a hematopoietic cell, hereinafter a "hematopoietic cell targeting liposome" (HTL), comprising an antibody directed towards a molecule preferentially or uniquely expressed on activated lymphocytes. In an embodiment of the invention, the molecule is an extracellular domain of a cell adhesion molecule (CAM). The CAM may be an integrin. The integrin may be a high affinity conformation of lymphocyte-function-associated antigen-1 (LFA-1). The antibody may be present on the HTL's external surface. The antibody may optionally be an antibody portion that comprises an antigen binding region, for example an Fab fragment.

The HTL may further comprise an oligonucleotide capable of decreasing WASp gene expression. The oligonucleotide may be present within the internal cavity of the HTL. The HTL may be administered to a patient suffering from a hematopoietic malignancy. The HTL may be attracted to and fuse with a malignant hematopoietic cell, thereby introducing into the cell an oligonucleotide capable of decreasing WASp gene expression, thereby decreasing the malignancy of the malignant hematopoietic cell, thereby treating the hematopoietic malignancy.

The HTL may comprise an agent (hereinafter a WASp degrading agent) that increases WASp degradation. The WASp degrading agent may be a molecule, such as a small molecule, a peptide, or an oligonucleotide. The WASp degrading may be present within the internal cavity of the HTL. The HTL may be administered to a patient suffering from a malignancy associated with a hematopoietic cell. The HTL may be attracted to and fuse with a malignant hematopoietic cell, thereby introducing into the cell a WASp degrading agent increasing WASp degradation, thereby decreasing the malignancy of the malignant hematopoietic cell, thereby treating the hematopoietic malignancy.

According to an embodiment of the invention, the inventors further suggest targeting cells using a liposome for treating WAS and/or XLT. Cells having improper WASp expression, or insufficient WASp expression may be targeted by administering to a patient in need thereof a liposome, hereinafter known as a WAS cell targeting liposome, or WTL. The WTL may comprise a targeting moiety, such as an antibody directed towards a cell having improper or insufficient WASp expression. The antibody may be present on the WTL's external surface. The WTL may further comprise a WASp degradation prevention agent, which may be a molecule, such as a small molecule, oligonucleotide or a peptide capable of preventing or reducing degradation of WASp. The WASp degradation prevention agent may be present within the WTL's internal cavity. According to an embodiment of the invention, the WASp degradation prevention agent to WASp at a WASp degradation site.

According to an embodiment of the invention, the cell having improper WASp expression is leukocyte or another hematopoietic cell. According to an embodiment of the invention, the cell having improper or insufficient WASp expression is lymphocyte, dendritic cell, macrophage, monocyte, granulocyte, megakaryocyte or a platelet.

The antibody present on the WTL may be directed towards a molecule preferentially or uniquely expressed on a leukocyte, hematopoietic cell, lymphocyte, dendritic cell, macrophage, monocyte, granulocyte, megakaryocyte or a platelet. The antibody may be directed towards the extracellular domain of a surface molecule or a CAM. The CAM may be an integrin. The antibody may be directed towards a surface molecule or an integrin in its low activity conformation. In an embodiment of the invention, the antibody is directed towards CD11c, CD123, CD56, CD34, CD14, CD33, CD66b, CD41, CD45, CD61, CD20, CD19, CD3, CD4, CD8, CD62 or an $\alpha_{IIb}\beta_3$ integrin.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical structures, elements or parts that appear in more than one figure are generally labeled with a same numeral in all the figures in which they appear. Dimensions of components and features shown in the figures are chosen for convenience and clarity of presentation and are not necessarily shown to scale.

DETAILED DESCRIPTION

Figure 1:
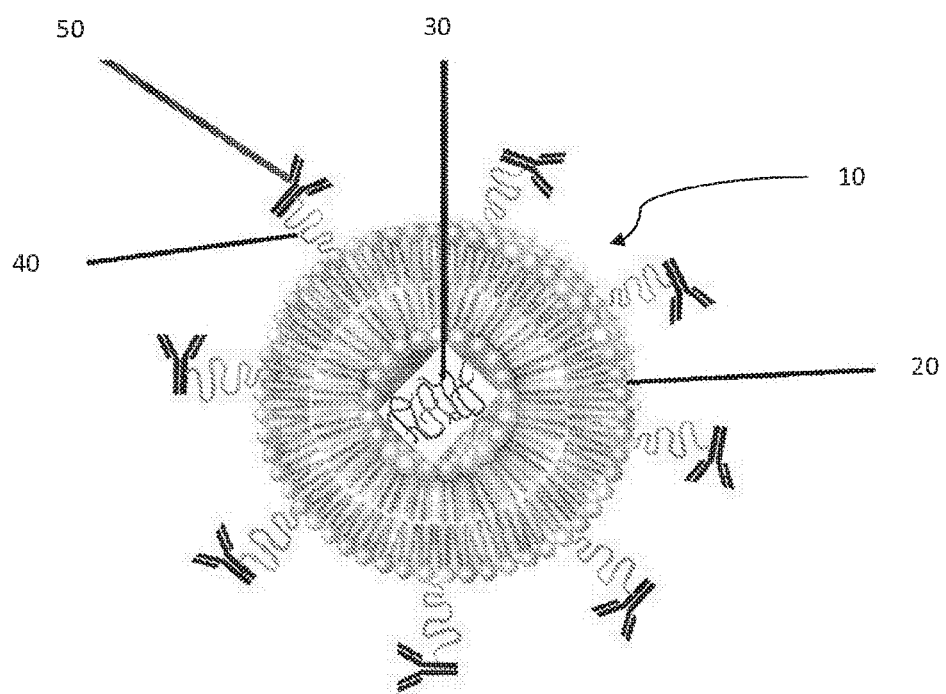
FIG. 1 schematically depicts a liposome according to an embodiment of the invention.

As mentioned in the summary above, HTL and WTL are both liposomes modified to target cells and to treat disease. A liposome 10 is schematically shown according to an embodiment of the invention in FIG. 1. Liposomes are substantially spherical vesicles comprising a lipid bilayer 20. Liposome 10 further comprises a therapeutic agent 30, a linker 40 and a targeting molecule 50.

According to an embodiment of the invention, lipid bilayer 20 comprises a phospholipid, preferably a neutral phospholipid. According to an embodiment of the invention, the phospholipid is phosphatidylcholine. According to an embodiment of the invention, the phospholipid is soybean phosphatidylcholine. According to an embodiment of the invention, the phospholipid is 1,2-dipalmitoyl-sn-glycero-3-phosphoethanolamine (DPPE).

Other neutral phospholipids that may be used are selected from the group consisting of:
1,2-dioleoyl-sn-glycero-3-phosphocholine (DOPC);
1,2-dioleoyl-sn-glycero-3-phosphoethanolamine (DOPE);
1,2-dimyristoylphopsphoetyhanolamine (DMPE);
1-palmitoyl-2-oleoyl-sn-glycero-3-phosphocholine (POPC); and
1,2-dipalmitoylphosphatidylcholine (DPPC).

According to an embodiment of the invention, the lipid bilayer comprises a mixture of more than one lipid. According to an embodiment of the invention, the lipid bilayer comprises a sterol, preferably cholesterol. According to an embodiment of the invention, the lipid bilayer is composed of phosphatidylcholine, DPPE and cholesterol. According to an embodiment of the invention, the ratio between phosphatidylcholine, DPPE and cholesterol is 6:2:2. According to an embodiment of the invention, the liposome 10 is a unilamellar vesicle.

According to an embodiment of the invention, liposomes 10 have an average diameter of between about 80 and 200 nanometers (nm). According to an embodiment of the invention, the liposomes of HTL and WTL have an average diameter of between about 90 to about 140 nm, without being bound to a targeting moiety. According to an embodiment of the invention, the liposomes of HTL and WTL have an average diameter of between about 100 and about 170 nm after being bound to a targeting moiety.

Therapeutic agent 30 may be a molecule, such as a small molecule, a peptide, a protein, or an oligonucleotide. Therapeutic agent 30 may be derived from naturally occurring peptides, proteins or nucleotides, or may be synthetic. Therapeutic agent 30 may be a peptide comprising naturally or non-naturally occurring amino acids, or combinations thereof.

According to an embodiment of the invention in which liposome 10 is an HTL, therapeutic agent 30 may be an oligonucleotide which reduces expression of WASp. The oligonucleotide may be a small interfering RNA (siRNA) which reduces expression of WASp. Additionally or alternatively, a therapeutic agent 30 may a short-hairpin RNA (shRNA) embedded within a plasmid vector or Micro-RNA (miRNA). According to an embodiment of the invention, the siRNA comprises an oligonucleotide having at least 90% similarity to a sequence in Table 1:

TABLE 1

| SEQ. ID. NO. | siRNA oligonucleotides Sequence | Complementary sequence |
|---|---|---|
| 1 | 5'-UGACUGAGUGGCUGAGUUA | 3'-ACUGACUCACCGACUCAAU |
| 2 | 5'-GACCUAGCCCAGCUGAUAA | 3'-CUGGAUCGGGUCGACUAUU |
| 3 | 5'-GAAUGGAUUUGACGUGAAC | 3'-CUUACCUAAACUGCACUUG |
| 4 | 5'-GCCGAGACCUCUAAACUUA | 3'-CGGCUCUGGAGAUUUGAAU |
| 5 | 5'-UGAGAUGCUUGGACGAAAA | 3'-ACUCUACGAACCUGCUUUU |
| 6 | 5'-GAAUCAGAGGCAAAGUGGA | 3'-CUUAGUCUCCGUUUCACCU |
| 7 | 5'-UCUCAGUUCUUUCACUCA | 3'-AGAGUCAAGAGAAGUGAGU |

According to an embodiment of the invention, the oligonucleotide may be siRNA comprising a duplex of SEQ ID NO. 1 and its complementary sequence. According to an embodiment of the invention, the oligonucleotide may be siRNA comprising a duplex of SEQ ID NO. 2 and its complementary sequence. According to an embodiment of the invention, the oligonucleotide may be siRNA comprising a duplex of SEQ ID NO. 3 and its complementary sequence. According to an embodiment of the invention, the oligonucleotide may be siRNA comprising a duplex of SEQ ID NO. 4 and its complementary sequence. According to an embodiment of the invention, the oligonucleotide may be siRNA comprising a duplex of SEQ ID NO. 5 and its complementary sequence. According to an embodiment of the invention, the oligonucleotide may be siRNA comprising a duplex of SEQ ID NO. 6 and its complementary sequence. According to an embodiment of the invention, the oligonucleotide may be siRNA comprising a duplex of SEQ ID NO. 7 and its complementary sequence.

As mentioned above, WASp, and WIP are expressed in hematopoietic cells and are cytoskeleton proteins involved in actin polymerization. In normally functioning cells, WASp is degraded through ubiquitylation on lysine residues 76 and 81, leading to degradation of WASp. WIP binds to WASp, protecting it from ubiquitylation, thereby protecting it from degradation. In WAS patients, due to the production of mutated WASp, WIP does not properly associate with WASp and as a result, WASp degradation occurs at a more rapid rate than in individuals in which WASp is expressed properly.

According to an embodiment of the invention in which liposome 10 is a WTL, therapeutic agent 30 may be an agent peptide which binds to WASp, preventing or decreasing its degradation. According to an embodiment of the invention, the agent is a molecule, such as a small molecule, an oligonucleotide or a peptide. The agent bind to WASp, preventing ubiquitylation on lysine residue 76 or lysine residue 81.

According to an embodiment of the invention, the peptide binds to WASp to prevent the proteolysis of WASp by the calpain cysteine-protease. WASp has seven potential sites sensitive to calpain cysteine-protease, four of which are located in the N-terminal WH1 domain of WASp.

According to an embodiment of the invention, approximately 1000 to 10,000 oligonucleotide molecules are present as therapeutic agent 30 in each liposome 10. According to an embodiment of the invention, approximately 3,400-5,200 oligonucleotide molecules are present as therapeutic agent 30 in each liposome 10.

Linker 40 may be connected to lipid bilayer 20 and to targeting molecule 50. Linker 40 may comprise polyethylene glycol. Linker 40 may comprise a glycosaminoglycan. The glycosaminoglycan may be hyaluronan. Hyaluronan may have a molecular weight of about 700 kilodaltons (kDa) or more. The ratio between glycosaminoglycan and lipid bilayer may be about 1:1 by volume. Glycosaminoglycans such as hyaluronan have a stabilizing effect to enable the liposomes to undergo lyophilization (freeze drying) and rehydration without impact the structure of the liposomes.

According to an embodiment of the invention, targeting molecule 50 may be an antibody. The antibody may be a monoclonal antibody. The antibody may be directed towards a molecule uniquely expressed on a specific cell type. A molecule "uniquely expressed" on a specific cell type refers to a molecule which is primarily present on the surface of a specific type of cell, and is generally not present, or is present at relatively low levels in other cell types in an organism. The cell type may be lymphocytes, activated lymphocytes, leukocytes, hematopoietic cells, megakaryocytes or platelets. The antibody may be directed towards an extracellular domain of a cell surface molecule or a cell adhesion molecule (CAM). A CAM is a protein located on a surface of a cell, the protein being involved in binding with another cell or with extracellular matrix. The CAM may be an integrin. Integrins are composed of two subunits known as the alpha and beta subunits. Multiple types of alpha units and beta units are known to exist in humans. Integrins are known to adopt three major conformational states: inactive (low affinity), active (high affinity), and ligand occupied, in which the integrin is bound to a ligand. Integrins undergo conformational changes when transformed from a low affinity to a high affinity state by "opening up" to allow for easier binding of the ligand.

According to an embodiment of the invention, about 20-70 antibody molecules are present as targeting molecule on every liposome 10.

According to an embodiment of the invention in which liposome 10 is an HTL, targeting molecule 50 may be an antibody directed towards a molecule uniquely expressed on lymphocytes, preferably on activated lymphocytes. The molecule may be a CAM that is expressed primarily by lymphocytes. The antibody may be directed towards lymphocyte-function-associated antigen-1 (LFA-1). The antibody may be directed towards a high affinity conformation of lymphocyte-function-associated antigen-1 (LFA-1). The antibody may be directed towards a β subunit or an α subunit, preferably to the β2-I subunit or the α L-I subunit. The antibody may bind to an epitope comprising the CPNKEKEC sequence, hereinafter, SEQ ID NO. 8, in particular, the Glu173 and Glu175 amino acids. The antibody may be mAb24 (HM2183), KIM127 or AL-57.

According to an embodiment of the invention in which liposome 10 is a WTL, targeting molecule 50 may be an antibody directed to a molecule that is expressed uniquely by a lymphocyte, dendritic cell, macrophage, monocyte, granulocyte, megakaryocyte or a platelet. The antibody may be directed towards a CAM, preferably to an extracellular domain of a cell adhesion molecule. The cell adhesion molecule may be an integrin. The antibody may be directed towards an integrin in its low affinity conformation. In an embodiment of the invention, the antibody is directed towards an $\alpha_{IIb}\beta_3$ integrin.

According to an embodiment of the invention, liposome 10 is manufactured using sonication and extrusion. Linker 40 may be conjugated to liposome 10 using a coupling agent such as 1-ethyl-3-(3-dimethylaminopropyl) carbodiimide) to form an amide bond. Therapeutic agent 30 may be introduced into liposome 10 through optional combination with protamine and mixing. Targeting molecule 50 may be conjugated to linker 40 through amine coupling, optionally using a coupling agent such as 1-ethyl-3-(3-dimethylaminopropyl)carbodiimide).

Further embodiments of the invention relate to methods of treatment of disease comprising administering to a patient in need thereof, HTL or WTL liposomes. HTL liposomes may be administered to treat malignancies, including but not limited to, hematopoietic malignancies. Malignancies treated may include Precursor B or Precursor T Acute Lymphocytic Leukemia (ALL), multiple myeloma, Chronic lymphocytic leukemia (CLL) and Non-Hodgkin's Lymphoma (NHL). WTL liposomes may be administered to treat patients suffering from WAS and/or XLT.

In an embodiment of the invention, liposomes are combined with at least one pharmaceutically acceptable excipient to form a pharmaceutical composition. In an embodiment of the invention, the pharmaceutical composition is adapted for human or animal use via oral, rectal, vaginal, topical, nasal, ophthalmic, transdermal, subcutaneous, intramuscular, intraperitoneal or intravenous administration.

The pharmaceutical compositions according to an embodiment of the invention may be conveniently presented in unit dosage form and are prepared by any of the methods well known in the art of pharmacy. In an embodiment of the invention, the unit dosage form is in the form of a tablet, capsule, lozenge, wafer, patch, ampoule, vial or pre-filled syringe.

The pharmaceutical compositions according to embodiments of the invention are generally administered in the form of a pharmaceutical composition comprising at least one active component together with a pharmaceutically acceptable carrier or diluent.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the components of this invention can be combined with various sweetening agents, flavoring agents, coloring agents, emulsifying agents and/or suspending agents, as well as such diluents as water, ethanol, propylene glycol, glycerin and various like combinations thereof.

The compositions according to embodiments of this invention may also be administered in a controlled release formulation such as a slow release or a fast release formulation. Such controlled release dosage composition may be prepared using methods well known to those skilled in the art.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

Pharmaceutical compositions according to embodiments of the invention may contain an active amount of 0.1%-95% of liposome, preferably 1%-70%.

In an embodiment of the invention, the dosage of liposome is between 0.001 mg/kg and 10 mg/kg. The dosage may be administered daily, three times a week, or once a week.

According to an embodiment of the invention, liposomes are administered to a patient in need thereof in combination with an additional anti-cancer agent. In an embodiment of the invention, the anti-cancer agent is selected from the group consisting of doxorubicin, asparaginase, methotrexate, cytarabine, denileukin difitox, rituximab, daunorubicin, 0, cyclophosphamide, vincristine, fludarabine and dexamethasone.

Embodiments of the invention will be further described in the examples below.

Example 1A: Overexpression of WASp and WIP in Hematopoietic Malignant Cells

Molecular changes in the expression of WASp and WIP were examined by comparing WASp and WIP expression in human cancerous cells relative to normal peripheral blood lymphocytes (PBLs). Malignant cell-lines were derived from hematopoietic malignancies. PBLs were isolated from whole blood of healthy donors, using Ficol gradient, followed by expansion of the lymphocytes using phytohaemagglutinin (PHA) and interleukin-2. The cells were lysed using Tris-containing lysis buffer. Protein lysates were resolved on sodium dodecyl sulfate-polyacrylamide gel electrophoresis (SDS-PAGE), transferred to a nitrocellulose membrane, and immunoblotted with appropriate primary antibodies (mouse anti-WASp or Rabbit anti-WIP or mouse anti-GAPDH) Immunoreactive proteins were detected with either anti-mouse or anti-rabbit horseradish peroxidase-coupled secondary antibody followed by detection with enhanced chemiluminescence. A 2 to 6-fold overexpression of WASp and WIP was detected in cell extracts derived from various malignant hematopoietic cells including ALL, CLL and NHL. Notably, overexpression of both proteins is strongly correlated. These results indicate that targeting lymphocytes in which WASp and WIP expression is increased and interfering with WASp and WIP overexpression may be useful therapy of hematopoietic malignancies.

Example 1B: WASp Overexpression Upregulates Hematopoietic Cell Invasion

Effects of WASp on cell invasion were tested using a gelatinase-based assay. Lymphocytes transfected with a WASp-encoding plasmid expressed two-fold levels of WASp, and exhibited increased gelatinase activity as opposed to cells transfected with a control plasmid in which WASp expression levels were not doubled. Gelatinase activity represents ECM degradation, which typically accompanies cell invasion. ECM degradation was co-localized with accumulation of F-actin as shown by Phalloidin staining. These results show that WASp overexpression is related to increased cellular invasion ability. Decreasing WASp expression in malignant cells may decrease the cells' invasion ability, thereby reducing malignant metastases.

Example 1C: WASp Accumulation Enhances Lymphocytes Migration

Real-time imaging of activated yellow fluorescent protein (YFP) WASp-expressing cells was performed, comparing between wild type WASp-expressing cells to cells expressing accumulating non-degrading mutant WASp, truncated at its N' terminus. The cells were monitored using a confocal microscope, equipped with appropriate lasers, filters and detectors. Cells expressing mutant WASp did not spread normally; instead they rolled and migrated continuously. They did not form flat membrane structures (lamellipodia) but instead produced spike-like membrane protrusions (filopodia), which characterize migrating cancerous cells. These results further show that WASp accumulation in cells may be associated with presence of cancerous cellular structures in those cells. By controlling WASp expression using HTLs, malignant features may be reduced.

Example 1D: WASp Accumulation Enhances Lymphocyte Activation

Lymphocytes as described in Example 1C were used to assess the effect of WASp accumulation on lymphocyte activation, by measuring intracellular calcium concentration and the activity of the transcription factor, nuclear factor of activated T-cells (NFAT), which are indicators of lymphocyte activation and proliferation, respectively. Calcium levels were determined using spectrofluorometry using calcium sensitive Fluo-3 fluorophore and through cotransfection with an NFAT luciferase reporter plasmid. Significant increase in both intracellular calcium concentration and NFAT levels were shown in cells in which mutant YFP-WASp was expressed and accumulated. The results indicate that WASp accumulation in lymphocytes may increase lymphocyte activation and proliferation.

Example 1E: WASp Expression is Efficiently Gene-Silenced Following Treatment with Specific WASp siRNA As shown in the previous examples, WASp is overexpressed in malignant cells. Gene silencing of WASp expression using siRNA was tested. WASp was silenced using commercially available siRNA oligonucleotides. A mixture of the following oligonucleotides, each in the form of double-stranded siRNA duplex with its corresponding sequence at an amount of 500 pico-mole was introduced to $1\times10^7$ cells:

5'-GCCGAGACCUCUAAACUUA-3', (SEQ ID NO. 4)

5'-UGACUGAGUGGCUGAGUUA-3', (SEQ ID NO. 1)

5'-GAAUGGAUUUGACGUGAAC-3' (SEQ ID NO. 3)
and

5'-GACCUAGCCCAGCUGAUAA-3'. (SEQ ID NO. 2)

These experiments were performed in T cell leukemic cells. Silencing efficiency of about 90% was achieved 48 hours after transfection, when compared to non-specific (N.S) siRNA-treated cells.

This example indicates that siRNA, when introduced into malignant hematopoietic cells, is effective in reducing WASp expression, and may be useful in preventing spread and metastases of the malignancy. HTL according to embodiments of the invention may be used to target malignant hematopoietic cells and to introduce siRNA into them.

Example 2A: Manufacture of Liposomes According to Embodiments of the Invention

Liposomes coated with antibodies for use as HTL or WTL may be made as follows. In the first step, multilamellar vesicles (MLVs) composed of phosphatidylcholine (PC), Cholesterol (Chol) and 1,2-dipalmitoyl-sn-glycero-3-phosphoethanolamine (DPPE) at molar ratios of 6:2:2 (or alternatively, 6:2:1.9 with the addition of 0.1% DPPE labeled with Rhodamine fluorophore, for detection) are prepared. Lipid mixture is dissolved in chloroform to a final concentration of 2 milligrams per milliliter (mg/ml), by stirring for 35-40 minutes (min), at 60 degrees Celsius (° C.). This is followed by vacuum rotary evaporation for 30 min at 65° C. The lipid mixture is further dried in a vacuum desiccator, overnight. The resulted dry lipid film is hydrated with diluted phosphate buffered saline (PBS) at a pH of 7.4, thoroughly vortexed and then mixed, using an orbital shaker at 200 revolutions per minute (rpm) for 2 h at 37° C., to create MLVs.

The MLVs are then undergo 7 cycles of rapid freezing-thawing, using liquid nitrogen and a thermo-block set to 65° C., and then extruded with a hand-operated extrusion device at 65° C., to achieve unilamellar vesicles (ULVs) with a final size of ~100 nanometers (nm) in diameter. The extrusion is carried in two steps, using progressively decreasing pore-size polycarbonate membranes, from 0.2 to 0.1 micrometer (μm), with 10 cycles per pore-size, to form ULVs.

Linker (comprising hyaluronan) is conjugated to ULVs by dissolving 1 mg hyaluronan (HA; molecular weight-700 kDa) by stirring (37° C. for 30 min) in 0.1 molar (M) sodium acetate buffer. HA is then pre-activated with 20 mg of coupling agent 1-ethyl-3-(3-dimethylaminopropyl)carbodiimide (EDAC, pH=4.0) by stirring for 2 h at 37° C. The extruded ULV suspension is then ultracentrifuged for 1-3 h, followed by re-suspension of the pellet in 0.1 M borate buffer (pH=8.6). ULV suspension and activated HA are combined at a 1:1 by volume ratio and incubated overnight at 37° C., with gentle stirring. Free HA is separated from HA-ULVs by 3 washes, using an ultra-centrifuge ($10^5$ g, 4° C., for 1 h for each wash).

Coupling of monoclonal antibody (mAb) to HA-coated liposomes is performed (using an amine-coupling method) as follows. 50 microliters (μl) of HA-coated liposomes are activated by incubation with 200 μl of 400 mM EDAC and 200 μL of 100 mM N-Hydroxysuccinimide (NHS) for 20 min at room temperature, with gentle stirring. The NHS-EDAC-activated HA-liposomes are mixed with 50 μl (~25 μg) of the desired mAb (0.5 mg/ml in PBS, pH=7.4), followed by overnight incubation at room temperature with gentle stirring. An exemplary antibody which may be used for HTL includes KIM127 or mAb24 (HM2183). KIM127 has been previously described in the following, incorporated by reference: Stephens P, Romer J T, Spitali M, Shock A, Ortlepp S, Figdor C G, Robinson M K. KIM127, an antibody that promotes adhesion, maps to a region of CD18 that includes cysteine-rich repeats. Cell Adhes Commun. 1995 December; 3(5):375-84. PubMed PMID: 8640375. Lu C, Ferzly M, Takagi J, Springer T A. Epitope mapping of antibodies to the C-terminal region of the integrin beta 2 subunit reveals regions that become exposed upon receptor activation. J Immunol 2001 May 1; 166(9):5629-37. PubMed PMID: 11313403. For WTL, either antibodies against LFA-1 (for lymphocytes) or antibodies that recognizing megakaryocytes and platelets-specific αIIbβ3 integrins (CD41) may be used. The reactive residues are blocked with 20 μl ethanolamine HCl (1 M; pH=8.5).

The resulting liposomes are purified using a size exclusion column packed with sepharose CL-4B beads (Sigma-Aldrich, Saint Louis, Mo.) and equilibrated with HEPES-based buffer solution (HBS, pH=7.4), removing unbound mAbs.

The purified liposome suspensions are snap frozen in 200 μl aliquots in a mixture of 100% ethanol and dry ice for ~20-30 min, followed by freezing for 2-4 h at −80° C. The frozen aliquots are then lyophilized for 48 h using a lyophilizer device. The lyophilized liposomes are stored at −80° C. until further use.

Particle size distribution and zeta potential measurements: Particle size distribution and mean diameter of the antibody-coated liposome and control, non-coated liposomes are measured using a zeta potential and dynamic light scattering instrument according to the manufacturer instructions. All measurements are done in PBS (pH=7.4) at room temperature.

The size of liposomes formed according to the above method without antibody was 103.03±0.92 nm in diameter; and with antibody 138.29±0.27 nm in diameter. Zeta potentials for liposome without antibody and without HA were −8.1±0.51 millivolt (mV); without antibody and with HA were −17.8±1.2 mV; and with antibody and HA: −24.1±2.9 mV.

Therapeutic agent (peptide, small molecule or oligonucleotide) encapsulation and quantification of the efficiency of entrapment is performed as follows: The lyophilized liposomes (10-100 µg total lipids) are hydrated with 200 µl Diethylpyrocarbonate (DEPC) treated water with or without siRNAs (50-750 picomol). The siRNAs are mixed with full-length recombinant protamine (1:5, siRNA:protamine molar ratio), in nuclease free water, followed by incubation for 20 min at room temperature to form a complex. The lipospmes are shaken gently for 30 min at room temperature. Unencapsulated siRNA are removed via ultra-fast centrifugation (6.4×g, 4° C., 20 min) prior to adding the suspension to the cells. siRNA encapsulation efficiency is determined by the Quant-iT RiboGreen RNA assay (Invitrogen) according to the manufacturer's instructions. Entrappment efficiency is determined by comparing fluorescence of the RNA binding dye RiboGreen in the liposomes, in the presence and absence of a detergent, Triton X-100. In the absence of detergent, fluorescence is measured from accessible (unentrapped) siRNA only. Whereas, in the presence of the detergent fluorescence is measured from total siRNA. The % encapsulation is calculated by the equation:

$$\% \; siRNA \; \text{encapsulation} = \left[1 - \left(\frac{\text{free } siRNA \text{ conc.}}{\text{total } siRNA \text{ conc.}}\right)\right] \times 100.$$

Encapsulation percentage is about 60-95% encapsulation.

For peptide loading, the lyophilized liposomes (10-100 µg total lipids) are hydrated with 200 µl PBS containing the peptide (At phospholipid:peptide molar ratio of 250:1), and hydrated at 40° C. for 1 h by repeated vortexing. Peptide loading is quantified using fluorescently-labeled peptide (labeled with Cy3, Pep(Cy3)) and separation is performed by gel filtration chromatography using a Sephadex G 75 column. Pep(Cy3) is eluted as a single band together with the liposomes (liposome associated peptide). In comparison, free Pep(Cy3) used as control, do not show a single band, but smear along the column. The liposome-associated fraction is collected and quantified with the use of a spectrofluorometer in comparison to a sample that contains non-separated (total) Pep(Cy3). The % encapsulation is calculated by the equation:

$$\% \; \text{peptide encapsulation} = \left[\frac{\text{liposome associated } Cy3 \text{ intensitiy}}{\text{total } Cy3 \text{ intensity}}\right] \times 100.$$

Example 2B: Compounds which Modulate WASp Expression

Compounds were obtained and from ChemBridge Corporation. San Diego, Calif., USA. Of the compounds obtained, 14 were considered potential agents for modulating WASp expression, by their potential to bind to WASp. The 14 compounds were tested in 293T cells using the following procedure.

The compounds were individually dissolved in DMSO to make a stock solution of 20 millimolar (mM) and kept stored at −20° C. 293T cells were prepared to mid log phase, ~60-80% confluence, and were transfected with 15 µg of yellow-fluorescent protein, YFP-WASp plasmid (6023), using a Calcium-phosphate transfection protocol. Cells were collected and counted. $1\text{-}2 \times 10^6$ cells per sample in 6-well supplemented with 2-4 ml complete (10% FCS) DMEM medium ($0.5 \times 10^6$ cells/ml). Cells were plated in 6 wells ($0.5 \times 10^6$ cells/ml×Number of samples) and pre-incubate at 37°, 5% $CO_2$ for at least 4 h (for the cells to adhere. 1 ml of the medium in which the cells were grown is taken, and added to the compound (10-80 µM). The medium, with the compound, was added back to the cells in the plate, dropwise. Cells were incubated overnight at 37° C., 5% $CO_2$. Densitometric analysis of YFP-WASp expression in the cells treated with the compounds, using Western blot analysis. The compounds with a relative 1.5-fold change (either increase or decrease) of expression relative cells which were exposed to DMSO solvent control, are listed in table 2 below. Table 2 lists the compounds' modulation of WASp expression levels as a function of relative expression of WASp in relation to control.

TABLE 2

| Cmpd # | Chemical name | Structure |
|---|---|---|
| 4 | 4-[1-({6-[3-(methoxymethyl)pyrrolidin-1-yl]pyridin-3-yl}carbonyl)piperidin-4-yl]morpholine | 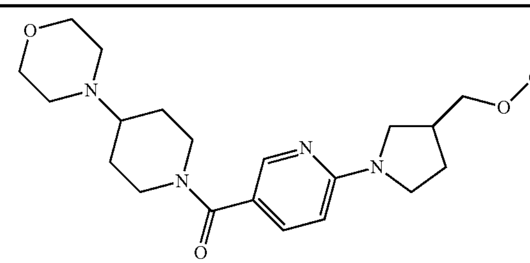 |
| 6 | N-[(2R,4R,6S)-2-(4-chlorophenyl)-6-(1-methyl-1H-1,2,3-benzotriazol-5-yl)tetrahydro-2H-pyran-4-yl] acetamide | 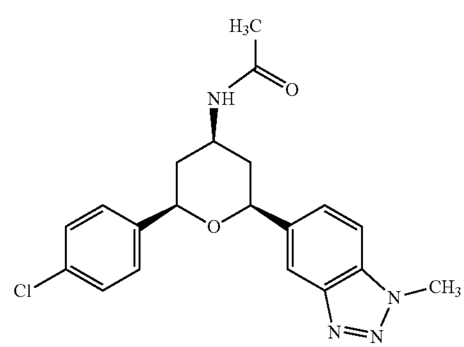 [SMILES: CC(=O)N[C@H]1C[C@@H](c2ccc3c(c2)nnn3C)O[C@@H](c2ccc(Cl)cc2)C1] |

TABLE 2-continued

| Cmpd # | Chemical name | Structure |
|---|---|---|
| 7 | 3,5-dimethyl-1-(1-{[5-(phenoxymethyl)-1H-pyrazol-3-yl]carbonyl}pyrrolidin-3-yl)-1H-pyrazole | 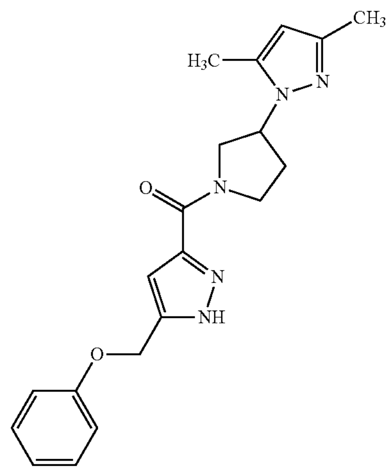 [SMILES: Cc1cc(C)n(C2CCN(C(=O)c3cc(COc4ccccc4)[nH]n3)C2)n1] |
| 10 | 4-{3-[(3-isopropyl-1,4,6,7-tetrahydro-5H-pyrazolo[4,3-c]pyridin-5-yl)carbonyl]phenyl}-2-methylbut-3-yn-2-ol | 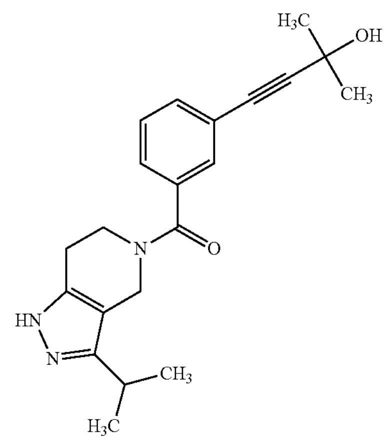 [SMILES: CC(C)c1n[nH]c2c1CN(C(=O)c1cccc(C#CC(C)(C)O)c1)CC2] |
| 13 | 8-(2,3-dihydro-1H-inden-2-yl)-1-isobutyl-3-(4-methoxybenzyl)-1,3,8-triazaspiro[4.5]decane-2,4-dione | 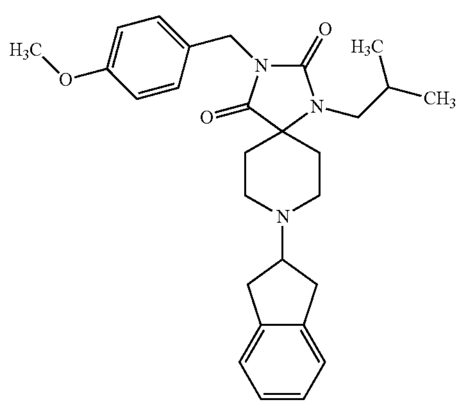 [SMILES: COc1ccc(CN2C(=O)N(CC(C)C)C3(CCN(C4Cc5ccccc5C4)CC3)C2=O)cc1] |

TABLE 2-continued

| Cmpd # | Chemical name | Structure |
|---|---|---|
| 14 | 2'-methoxy-N-(1-methyl-2-pyridin-2-ylethyl)biphenyl-3-carboxamide | 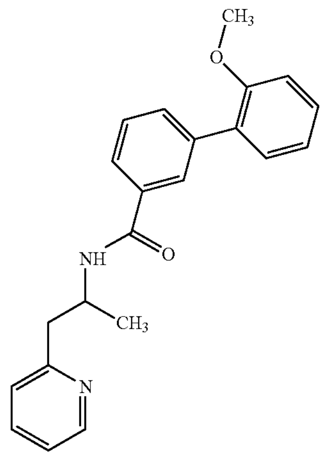 [SMILES: COc1ccccc1-c1cccc(C(=O)NC(C)Cc2ccccn2)c1] |

TABLE 3

| Compound Number | Relative expression |
|---|---|
| 4 | 1.5 |
| 6 | 6.7 |
| 7 | 2.1 |
| 10 | 0.6 |
| 13 | 0.3 |
| 14 | 0.5 |

This example shows that compounds 4, 6 and 7, increase WASp expression in cells. These compounds and/or WTL comprising these compounds may be used in treating WAS or other diseases.

The example also shows that compound 10, 13 and 14 are effective in decreasing WASp expression in cells. These compounds and/or WTL comprising these compounds may be used in treating malignancies.

Additional compounds which may be used include the compounds listed in table 4:

TABLE 4

| Compound # | Chemical name | Structure |
|---|---|---|
| 1 | 1-(3-methylphenyl)-2-(3-pyridinylmethyl)-2,3,4,9-tetrahydro-1H-beta-carboline | 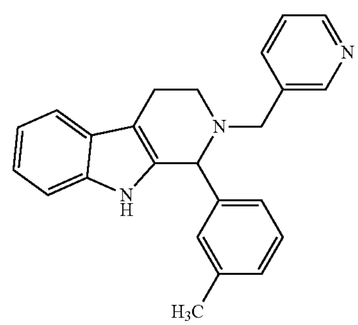 [SMILES: Cc1cccc(C2c3[nH]c4ccccc4c3CCN2Cc2cccnc2)c1] |
| 2 | N-[cyclopropyl(4-methylpyridin-2-yl)methyl]-3-methyl-1-propyl-1H-pyrazole-4-carboxamide | 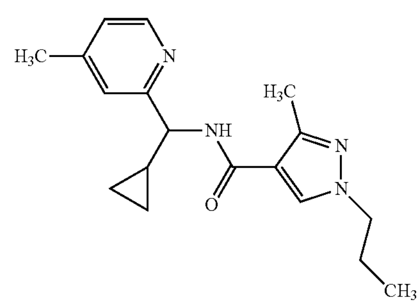 [SMILES: CCCn1cc(C(=O)NC(c2cc(C)ccn2)C2CC2)c(C)n1] |

TABLE 4-continued

| Compound # | Chemical name | Structure |
|---|---|---|
| 3 | N-(1,4-dimethyl-1H-pyrazol-5-yl)-3-{[(2S)-2-(methoxymethyl)pyrrolidin-1-yl]methyl}benzamide | 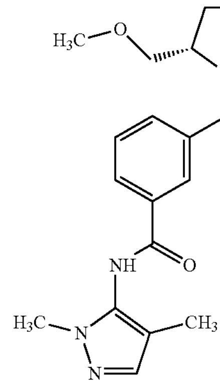 |
| 5 | 1-[(2E)-3-phenyl-2-propen-1-yl]-4-[2-(3-pyrrolidinyl)benzoyl]piperazine | 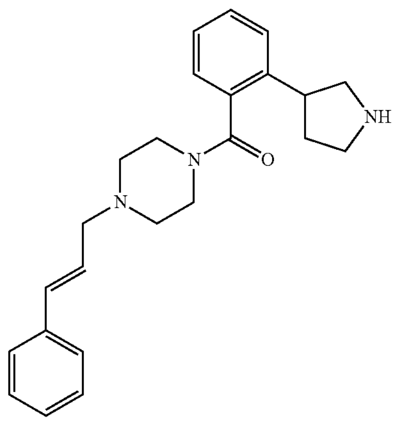 [SMILES: O=C(c1ccccc1C1CCNC1)N1CCN(C/C=C/c2ccccc2)CC1] |
| 8 | 4-(5-methylpyridin-2-yl)-1-[(5-methyl-1-pyridin-2-yl-1H-pyrazol-4-yl)carbonyl]piperidin-4-ol | 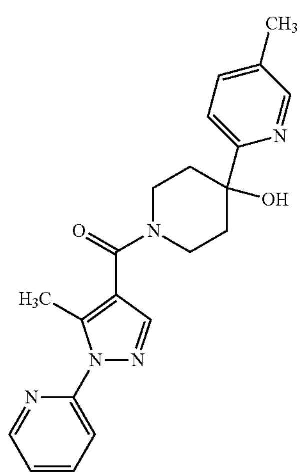 [SMILES: Cc1ccc(C2(O)CCN(C(=O)c3cnn(-c4ccccn4)c3C)CC2)nc1] |

TABLE 4-continued

| Compound # | Chemical name | Structure |
|---|---|---|
| 9 | N-(3-methylbenzyl)-N'-{[1-(pyridin-2-ylmethyl)pyrrolidin-3-yl]methyl}urea | 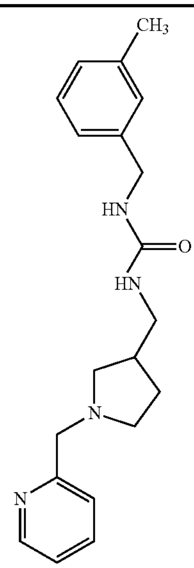 |
| 11 | 5-acetyl-N-(2-methylbenzyl)-N-(tetrahydrofuran-2-yl methyl)-4,5,6,7-tetrahydro-pyrazolo[1,5-a]pyrazine-2-carboxamide | 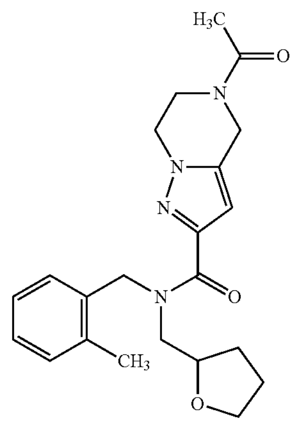 [SMILES: CC(=O)N1CCn2nc(C(=O)N(Cc3ccccc3C)CC3CCCO3)cc2C1] |
| 12 | 3-[(2,2-dimethylpropanoyl)amino]-2-methyl-N-[(1-methyl piperidin-3-yl)methyl]benzamide | 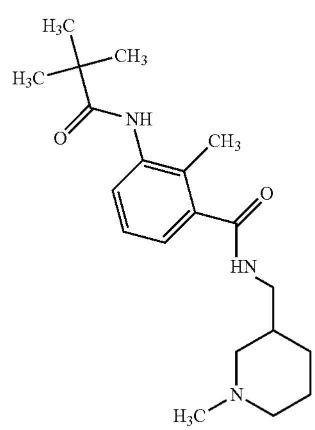 [SMILES: Cc1c(NC(=O)C(C)(C)C)cccc1C(=O)NCC1CCCN(C)C1] |

Example 2C: siRNA that Reduce the Expression of WASp

A number of siRNA duplexes were tested in cells as in example 1E. The following double-stranded siRNA sequences were used: SEQ ID NO. 1 and its complementary sequence; SEQ ID NO. 2 and its complementary sequence; SEQ ID NO. 3 and its complementary sequence; SEQ ID NO. 1 and its complementary sequence (designated as 1-4). 500 picomole of each double-stranded siRNA was used. In addition, a nonsense siRNA sequence (designated as "N.S. siRNA") was used as a control. Control N.S. siRNA was made from 125 duplexes of each of the siRNA molecules in Table 5:

TABLE 5

| SEQ ID NO. | Sequence |
|---|---|
| 9 | 5'-UAGCGACUAAACACAUCAAU AGGCUAUGAAGAGAUAC |
| 10 | 5'-AUGUAUUGGCCUGUAUUAG |
| 11 | 5'-AUGAACGUGAAUUGCUCAA |
| 12 | 5'-UGGUUUACAUGUCGACUAA |

Figure 2:
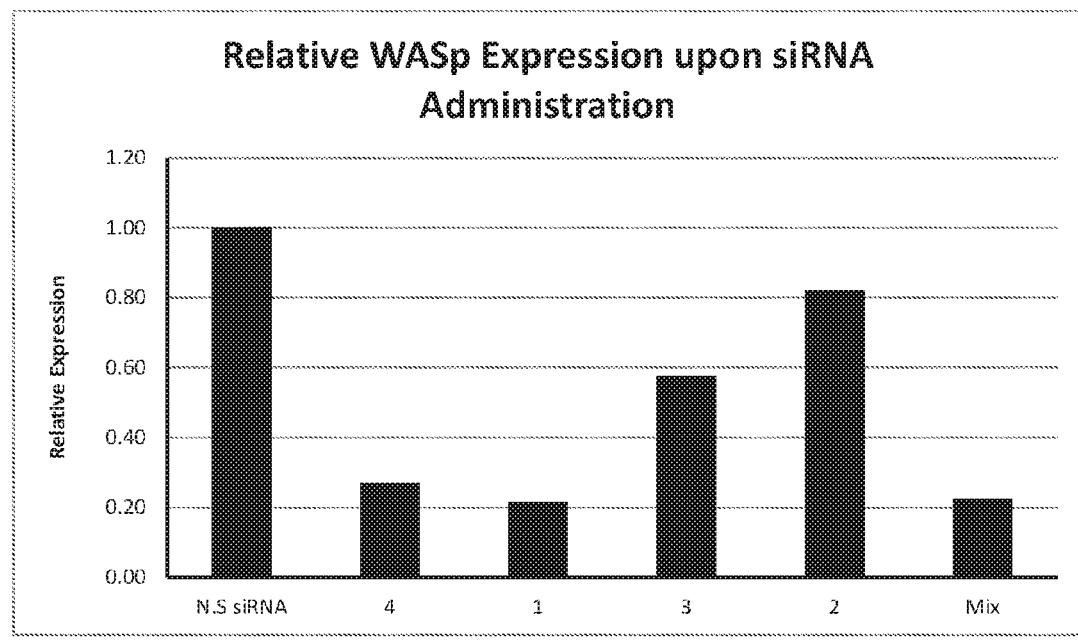
FIG. 2 shows a bar graph showing relative WASp expression upon administration of siRNA according to embodiments of the invention.

In addition, a mixture of the siRNAs comprising SEQ ID NOS. 1-4 (designated as "Mix") was also used, comprising 125 picomole of each. Upon analysis with Western blot, it was shown that all siRNA duplexes were effective in down-regulating WASp, with the siRNA of SEQ. ID NO. 1 being the most effective single siRNA used. N.S. siRNA was ineffective in downregulating WASp. A bar chart detailing the relative expression of WASp relative to control (non-treated) cells is shown in FIG. 2.

Example 2D: WIP-Inspired Peptides

According to embodiments of the invention, WIP-inspired peptides may be made. WIP inspired peptides are peptides which are similar to sections of naturally occurring WIP peptide, with potential modifications. According to an embodiment of the invention, the WIP inspired peptides have 90% similarity to the corresponding section of naturally occurring WIP. According to an embodiment of the invention, WIP-inspired peptides bind to WASp at lysine residues 76 and 81, which have been observed to be sites of ubiquitylation of WASp. Without being bound by theory, it is suggested that WIP-inspired peptides bind to these lysine residues of WASp, thereby protecting WASp from ubiquitylation, and subsequent degradation.

WIP inspired peptides are made using the following method. A maltose-binding protein (MBP) fusion construct containing a $His_6$-tag for purification and a tobacco etch virus (TEV) protease site was employed to efficiently express WIP-inspired peptides. The MBP-His-Tev-peptide coding sequence amplified in *E. coli* DH5α cells, and transformed into BL21(DE3) expression cells. WIP-inspired peptides were expressed in M9 minimal medium using standard protocols. Cells were grown at 37° C. until an $OD_{600}$ of about 0.8-1.0 was achieved. Isopropyl-thio-galactose (IPTG) was then added to a final concentration of 1.0 mM and induction proceeded at 27° C. overnight. Cells were centrifuged, re-suspended in lysis buffer (10 mM Tris buffer pH 7.5, 500 mM NaCl, 10 mM imidazole, 5 mM benzamidine, and 1 mM DTT). Cells were lysed by homogenization (C5 homogenizer, Avestin), followed by addition of a second aliquot of 5 mM benzamidine and 1 mM PMSF were added, and the lysate was clarified by centrifugation. Lysate was applied on a HiTrap Chelating HP column (GE Healthcare, Inc.) charged with $Ni^{2+}$, and after washing with lysis buffer the protein was eluted in lysis buffer containing 50 mM imidazole. Overnight dialysis against lysis buffer allowed TEV protease cleavage (added 1:40 w/w) for 3 h at 30° C. Immediately after cleavage, the reaction was loaded again on the column and the protein was collected in the flow-through which was then dialyzed overnight at room temperature against 20 mM Tris pH 7.5. Finally, the protein was applied on a cation exchange column equilibrated with 20 mM Tris, pH 7.5, 10 mM NaCl. The column was washed in 20 mM Tris, pH 7.5, 50 mM NaCl buffer, and eluted as the NaCl concentration was raised to 125 mM. The pH of the peptide-containing fraction was lowered to 3.0 using 1 M formate buffer to a final concentration of 50 mM, allowing the protein to be safely concentrated in a centrifugal concentration tube (MWCO 3 kDa, Vivaspin) to final volume of 0.5 mL. Serial dilutions and concentrations of the protein with 5 mM formate pH 3.0 were employed to remove phosphate and NaCl from the buffer. The pH was then adjusted to pH 5.8-7.0 and the resulting purified peptides were lyophilized and frozen at −80° C. for storage.

The following peptides in table 6 may be synthesized according to embodiments of the invention:

TABLE 6

| SEQ. ID NO: | Based on WIP residues | Sequence |
|---|---|---|
| 13 | 442-492 | MGSSHHHHHH SGQDSPCEDE WESRFYFHPI SDLPPPEPYV QTTKSYPSKL ARNESRSGSN PRE |
| 14 | 461-481 | DLPPPEPYVQ TTKSYPSKLA R |
| 15 | 442-485 | MGSSHHHHHH SGQDSPCEDE WESRFYFHPI SDLPPPEPYV QTTKSYPSKL ARNESR |

It is suggested that these peptides may bind lysine residues 76 and/or 81 of WASp, thereby protecting WASp from ubiquitylation and subsequent degradation.

Example 3A: Use of WTL in Treating WAS In Vivo

WAS knockout mice are used. Wild type (WT) littermates are used as controls. Mice are housed under pathogen-free conditions. Suspensions (200 μl) of liposomes comprising peptides which binds to WASp at a WASp degradation sites, and prevent the degradation of WASp, either by ubiquitylation or by calpain-mediated proteolysis, are sonicated in a bath sonicator for 5 min, and immediately intravenously injected via tail veins. Body weight and clinical symptoms are monitored daily. Mice are sacrificed on day 9 and the spleen is removed. Lymphocytes and megakaryocyte cell lineage are purified and analyzed for WASp expression levels.

Treatment with WTL may increase amount of WASp properly expressed in WAS knockout mice. Clinical symptoms may be improved in mice treated with WTL relative to control mice.

Example 3B: Use of HTL in Treating Malignancies In Vivo

Female NOD/SCID (NOD/LtSz-scid/scid) mice aged 5 to 6 weeks are purchased and housed in a pathogen free environment. On the day of inoculation, mice receive 250 centigeiger (cGy) of total body irradiation at a dose rate of 325 cGy/min by parallel opposed 4MV x-rays Immediately prior to inoculation, mice are warmed by infrared lamp, then inoculated by tail-vein injection with between 2.5–10×10$^6$ leukemia cells in a maximum volume of 100 mL PBS. Mice are monitored every 14 days for leukemia engraftment by staining approximately 50 mL peripheral blood taken from the tail vein with anti-CD45 (leukocyte common antigen, Ly-5) antibodies, FITC-conjugated anti-murine and PE-conjugated anti-human CD45. Following lysis of erythrocytes with ammonium chloride, samples are analyzed by flow cytometry. The proportion of human versus murine CD45 cells are calculated. This parameter has been shown to accurately reflect the overall leukemic burden. This method should detect 1% human CD45 cells in murine peripheral blood.

Continuous xenografts are established by harvesting human leukemia cells from the spleens of engrafted mice, exactly as described above. Preparations of T-ALL cells are used to establish continuous childhood ALL xenografts from mouse spleens routinely consisted of more than $3 \times 10^8$ cells per spleen at more than 85% purity. Prior to inoculation into secondary or tertiary recipient mice, cells are thawed rapidly in RPMI 1640 medium containing 20% fetal bovine serum (FBS).

For a comparison of rates of secondary and tertiary engraftment with the rate of primary engraftment, equal numbers of human leukemia cells are inoculated in each case. Administration HTLs may show improvement in overall leukemic burden.

There is further provided, according to an embodiment of the invention, a liposome comprising: a lipid bilayer having an internal cavity; a therapeutic agent within the internal cavity configured to modify expression or degradation of WASp in a cell; and a targeting moiety external to the lipid bilayer configured to target an extracellular domain of a cell. Optionally, the targeting moiety comprises an antibody. Optionally, the targeting moiety comprises an agent which binds a molecule preferentially or uniquely expressed on the surface of a hematopoietic cell. Optionally, the hematopoietic cell is a lymphocyte. Optionally, the molecule on the hematopoietic cell surface is selected from the group consisting of: a cell adhesion molecule and an integrin. Optionally, the integrin is a high affinity conformation of lymphocyte-function-associated antigen-1. Optionally, the therapeutic agent is selected from the group consisting of a small molecule, a peptide or an oligonucleotide. Optionally, the therapeutic agent binds to WASp. Optionally, the therapeutic agent, when contacted with a cell which expresses WASp, reduces the expression of WASp in the cell. Optionally, the therapeutic agent comprises siRNA, shRNA or miRNA. Optionally, the siRNA comprises an oligonucleotide having the sequence of SEQ ID NO. 1, SEQ ID NO. 2, SEQ ID NO. 3, SEQ ID NO. 4, SEQ ID NO. 5, SEQ ID NO. 6 or SEQ ID NO. 7, and a complementary strand associated to the oligonucleotide. Optionally, the targeting moiety comprises an agent which binds a molecule uniquely or preferentially expressed on the surface of a leukocyte, hematopoietic cell, megakaryocyte or a platelet. Optionally, the molecule is selected from the group consisting of: a cell adhesion molecule and an integrin. Optionally, the integrin is in its low activity conformation. Optionally, the targeting moiety comprises an agent which binds an αIIbβ3 integrin. Optionally, the therapeutic agent is selected from the group consisting of a molecule, a peptide and an oligonucleotide. Optionally, the therapeutic agent binds to a WAS protein. Optionally, the therapeutic agent, when contacted with WASp, binds to a ubiquitylation site. Optionally, the ubiquitylation site is a lysine residue 76 or 81. Optionally, the therapeutic agent, when contacted with a cell which expresses WASp, reduces the degradation of WASp in the cell. Optionally, the therapeutic agent, when contacted with a cell which expresses WASp, reduces the proteolysis of WASp by calpain cysteine-protease. Optionally, the lipid bilayer comprises a phospholipid. Optionally, phospholipid comprises phosphatidylcholine or 1,2-dipalmitoyl-sn-glycero-3-phosphoethanolamine (DPPE). Optionally, the lipid bilayer comprises a sterol. Optionally, the sterol is cholesterol. Optionally, the lipid bilayer comprises phosphatidylcholine, DPPE and cholesterol. Optionally, the ratio of of phosphatidylcholine, DPPE and cholesterol in the bilipid layer is about 6:2:2. Optionally, the average diameter of the liposomes in a plurality of liposomes is between about 100 and about 170 nanometers. Optionally, the liposome further comprising a linker. Optionally, the linker comprises a glycosaminoglycan. Optionally, the glycosaminoglycan comprises hyaluronan. Optionally, the antibody binds an epitope comprising SEQ ID NO. 8. Optionally, the antibody is selected from the group consisting of: mAb24 (HM2183), KIM127 and AL-57. Optionally, the therapeutic agent is selected from the group consisting of: 4-[1-({6-[3-(methoxymethyl)pyrrolidin-1-yl] pyridin-3-yl}carbonyl)piperidin-4-yl]morpholine, N-[(2R,4R,6S)-2-(4-chlorophenyl)-6-(1-methyl-1H-1,2,3-benzotriazol-5-yl)tetrahydro-2H-pyran-4-yl]acetamide, 3,5-dimethyl-1-(1-{[5-(phenoxymethyl)-1H-pyrazol-3-yl]carbonyl}pyrrolidin-3-yl)-1H-pyrazole, 4-{3-[(3-isopropyl-1,4,6,7-tetrahydro-5H-pyrazolo[4,3-c]pyridin-5-yl)carbonyl]phenyl}-2-methylbut-3-yn-2-ol, 8-(2,3-dihydro-1H-inden-2-yl)-1-isobutyl-3-(4-methoxybenzyl)-1,3,8-triazaspiro[4.5]decane-2,4-dione, and T-methoxy-N-(1-methyl-2-pyridin-2-ylethyl)biphenyl-3-carboxamide. Optionally, the therapeutic agent is selected from the group consisting of: 1-(3-methylphenyl)-2-(3-pyridinylmethyl)-2,3,4,9-tetrahydro-1H-beta-carboline, N-[cyclopropyl(4-methylpyridin-2-yl)methyl]-3-methyl-1-propyl-1H-pyrazole-4-carboxamide, N-(1,4-dimethyl-1H-pyrazol-5-yl)-3-{[(2S)-2-(methoxymethyl)pyrrolidin-1-yl]methyl}benzamide, 1-[(2E)-3-phenyl-2-propen-1-yl]-4-[2-(3-pyrrolidinyl)benzoyl]piperazine, 4-(5-methylpyridin-2-yl)-1-[(5-methyl-1-pyridin-2-yl-1H-pyrazol-4-yl)carbonyl]piperidin-4-ol, N-(3-methylbenzyl)-N'-{[1-(pyridin-2-ylmethyl)pyrrolidin-3-yl]methyl}urea,5-acetyl-N-(2-methylbenzyl)-N-(tetrahydrofuran-2-ylmethyl)-4,5,6,7-tetrahydropyrazolo[1,5-a]pyrazine-2-carboxamide and 3-[(2,2-dimethylpropanoyl)amino]-2-methyl-N-[(1-methylpiperidin-3-yl)methyl]benzamide. Optionally the therapeutic agent comprises a peptide having a similarity of at least 90% human WIP, wherein the peptide binds to WASp at lysine residues 76 or 81. Optionally, the peptide comprises SEQ. ID NO. 13, 14 or 15.

There is further provided, according to an embodiment of the invention methods for the treatment of a disease in a patient comprising administering to a patient in need thereof a liposome according to any one of the previous claims. Optionally, the patient suffers from a malignancy. Optionally, the malignancy is a hematopoietic malignancy. Optionally, the hematopoietic malignancy is Precursor B or Precursor T Acute Lymphocytic Leukemia (ALL), multiple myeloma, Chronic lymphocytic leukemia (CLL) or Non-Hodgkin's Lymphoma (NHL). Optionally, the patient suffers from Wiskott-Aldrich syndrome or from X-linked thrombocytopenia.

There is further provided according to an embodiment of the invention, a pharmaceutical composition comprising a pharmaceutically acceptable carrier and a compound selected from the group consisting of: 4-[1-({6-[3-(methoxymethyl)pyrrolidin-1-yl] pyridin-3-yl}carbonyl)piperidin-4-yl]morpholine, N-[(2R,4R,6S)-2-(4-chlorophenyl)-6-(1-methyl-1H-1,2,3-benzotriazol-5-yl)tetrahydro-2H-pyran-4-yl]acetamide, 3,5-dimethyl-1-(1-{[5-(phenoxymethyl)-1H-pyrazol-3-yl]carbonyl}pyrrolidin-3-yl)-1H-pyrazole, 4-{3-[(3-isopropyl-1,4,6,7-tetrahydro-5H-pyrazolo[4,3-c]pyridin-5-yl)carbonyl]phenyl}-2-m ethylbut-3-yn-2-ol, 8-(2,3-dihydro-1H-inden-2-yl)-1-isobutyl-3-(4-methoxybenzyl)-1,3,8-triazaspiro[4.5]decane-2,4-dione, and 2'-methoxy-N-(1-methyl-2-pyridin-2-ylethyl)biphenyl-3-carboxamide.

There is further provided according to an embodiment of the invention a pharmaceutical composition comprising a pharmaceutically acceptable carrier and a compound selected from the group consisting of:

1-(3-methylphenyl)-2-(3-pyridinylmethyl)-2,3,4,9-tetrahydro-1H-beta-carboline,

N-[cyclopropyl(4-methylpyridin-2-yl)methyl]-3-methyl-1-propyl-1H-pyrazole-4-carboxamide, N-(1,4-dimethyl-1H-pyrazol-5-yl)-3-{[(2S)-2-(methoxymethyl)pyrrolidin-1-yl]methyl}benzamide, 1-[(2E)-3-phenyl-2-propen-1-yl]-4-[2-(3-pyrrolidinyl)benzoyl]piperazine, 4-(5-methylpyridin-2-yl)-1-[(5-methyl-1-pyridin-2-yl-1H-pyrazol-4-yl)carbonyl]piperidin-4-ol, N-(3-methylbenzyl)-N'-{[1-(pyridin-2-ylmethyl)pyrrolidin-3-yl]methyl}urea, 5-acetyl-N-(2-methylbenzyl)-N-(tetrahydrofuran-2-ylmethyl)-4,5,6,7-tetrahydropyrazolo[1,5-a]pyrazine-2-carboxamide and 3-[(2,2-dimethylpropanoyl)amino]-2-methyl-N-[(1-methylpiperidin-3-yl)methyl]benzamide.

There is further provided, according to an embodiment of the invention, a pharmaceutical composition comprising a pharmaceutically acceptable carrier and compound selected from the group consisting of: SEQ ID NO: 1, SEQ ID NO. 2, SEQ ID NO. 3, SEQ ID NO. 4, SEQ ID NO. 5, SEQ ID NO. 6 or SEQ ID NO. 7, and a complementary strand associated to the oligonucleotide.

There is further provided, according to an embodiment of the invention, a method for treating a person suffering from a disease, comprising administering the pharmaceutical composition as disclosed above. Optionally, the disease is a malignancy, Wiskott-Aldrich syndrome or X-linked thrombocytopenia.

There is further provided, according to embodiments of the invention, a peptide having a similarity of at least 90% human WIP, wherein the peptide binds to WASp at lysine residues 76 or 81, thereby protecting WASp from ubiquitylation and subsequent degradation. Optionally, the peptide comprising SEQ. ID NO. 13, 14 or 15.

There is further provided according to an embodiment of the invention, a method for the treatment of a disease in a patient comprising administering to a patient in need thereof a pharmaceutical composition comprising a peptide as described above. Optionally, the disease is a malignancy, Wiskott-Aldrich syndrome or X-linked thrombocytopenia.

In the description and claims of the present application, each of the verbs, "comprise," "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A liposome comprising:
    a lipid bilayer having an internal cavity;
    a therapeutic agent within the internal cavity, wherein said therapeutic agent is:
        (a) a WASp-specific siRNA that, when contacted with a cell, reduces the expression of WASp or increases WASp degradation in said cell, said siRNA comprising an oligonucleotide having the sequence of any one of SEQ ID NO: 1, SEQ ID NO: 2, SEQ ID NO: 3, SEQ ID NO: 4, SEQ ID NO: 5, SEQ ID NO: 6 and SEC) ID NO: 7, any complementary strand thereof, or a duplex of said oligonucleotide with its complementary strand, or any mixture of said siRNAs; or
        (b) a peptide that binds to WASp at lysine residues 76 or 81, wherein the peptide comprises SEQ ID NO: 13, 14, or 15, thereby protecting WASp from ubiquitylation and subsequent degradation; and
    a targeting moiety external to the lipid bilayer, said targeting moiety comprising an agent that binds a molecule preferentially or uniquely expressed on the surface of at least one of a hematopoietic cell, a leukocyte, megakaryocyte and a platelet.

2. The liposome according to claim 1, wherein the targeting moiety comprises an antibody.

3. The liposome according to claim 1, wherein the targeting moiety comprises an agent which binds a molecule preferentially or uniquely expressed on the surface of a hematopoietic cell.

4. The liposome according to claim 3, wherein the molecule on the hematopoietic cell surface is selected from the group consisting of: a cell adhesion molecule and an integrin.

5. The liposome according to claim 4, wherein the integrin is a high affinity conformation of lymphocyte-function-associated antigen-1.

6. A liposome comprising:
    a lipid bilayer having an internal cavity;
    a therapeutic agent within the internal cavity, wherein said therapeutic agent is a WASp-specific siRNA that, when contacted with a cell, reduces the expression of WASp or increases WASp degradation in said cell, said siRNA comprising an oligonucleotide having the sequence of any one of SEQ ID NO. 1, SEQ ID NO. 2, SEQ ID NO. 3, SEQ ID NO. 4, SEQ ID NO. 5, SEQ ID NO. 6 and SEQ ID NO. 7, any complementary strand thereof, or a duplex of said oligonucleotide with its complementary strand, or any mixture of said siRNAs.

7. The liposome according to claim 1, wherein the targeting moiety comprises an agent which binds a molecule uniquely or preferentially expressed on the surface of a leukocyte, megakaryocyte or a platelet, and wherein the targeting moiety is one that binds an integrin.

8. The liposome according to claim 7, wherein the therapeutic agent is a peptide of (b).

9. The liposome according to claim 8, wherein the therapeutic agent, when contacted with a cell which expresses WASp, reduces the degradation of WASp in the cell.

10. The liposome according to claim 1, wherein the lipid bilayer comprises phosphatidylcholine, DPPE and cholesterol.

11. A plurality of liposomes according to claim 1, wherein the average diameter of the liposomes is between about 100 and about 170 nanometers.

12. The liposome according to claim 6, wherein said siRNA comprises an oligonucleotide having the sequence complementary to SEQ ID NO. 1, SEQ ID NO. 2, SEQ ID NO. 3, SEQ ID NO. 4, SEQ ID NO. 5, SEQ ID NO. 6 or SEQ ID NO. 7, or a duplex of said oligonucleotide with its complementary strand, or any mixture of said siRNAs.

13. A WASp-specific siRNA that, when contacted with a cell, reduces the expression of WASp or increases WASp degradation in said cell, wherein said siRNA comprises an oligonucleotide having the sequence of SEQ ID NO. 6 or a duplex of said oligonucleotide with its complementary strand.

14. A WASp-specific siRNA that, when contacted with a cell, reduces the expression of WASp or increases WASp degradation in said cell, wherein said siRNA comprises an oligonucleotide having the sequence complementary to SEQ ID NO. 1, SEQ ID NO. 2, SEQ ID NO. 3, SEQ ID NO. 4, SEQ ID NO. 5, SEQ ID NO. 6 or SEQ ID NO. 7, or a duplex of said oligonucleotide with its complementary strand.

15. A pharmaceutical composition comprising a pharmaceutically acceptable carrier and a therapeutic agent that modifies expression or degradation of WASp in a cell, wherein said therapeutic agent is:
- (a) a WASp-specific sRNA that, when contacted with a cell, reduces the expression of WASp or increases WASp degradation in said cell, wherein said siRNA comprises an oligonucleotide having the sequence of SEQ ID NO. 6, a complementary sequence thereof, or a duplex of said oligonucleotide with its complementary strand; or
- (b) a peptide that binds to WASp at lysine residues 76 or 81, wherein the peptide comprises SEQ ID NO: 13, 14, or 15, thereby protecting WASp from ubiquitylation and subsequent degradation.

16. A pharmaceutical composition comprising a pharmaceutically acceptable carrier and a therapeutic agent that modifies expression or degradation of WASp in a cell, wherein said therapeutic agent is:
- (a) a WASp-specific sRNA that, when contacted with a cell, reduces the expression of WASp or increases WASp degradation in said cell, wherein said sRNA comprises an oligonucleotide having the sequence complementary to SEQ ID NO. 1, SEQ ID NO. 2, SEQ ID NO. 3, SEQ ID NO. 4, SEQ ID NO. 5, SEQ ID NO. 6 or SEQ ID NO. 7, or a duplex of said oligonucleotide with its complementary strand, or any mixture of said siRNAs; or
- (b) a peptide that binds to WASp at lysine residues 76 or 81, wherein the peptide comprises SEQ ID NO: 13, 14, or 15, thereby protecting WASp from ubiquitylation and subsequent degradation.

\* \* \* \* \*

UNITED STATES PATENT AND TRADEMARK OFFICE
CERTIFICATE OF CORRECTION

PATENT NO. : 11,266,601 B2
APPLICATION NO. : 16/933505
DATED : March 8, 2022
INVENTOR(S) : Mira Barda-Saad et al.

It is certified that error appears in the above-identified patent and that said Letters Patent is hereby corrected as shown below:

In the Claims

Claim 1, Column 31, Line 57, delete "SEC)" and insert --SEQ--

Claim 15, Column 34, Line 9, delete "sRNA" and insert --siRNA--

Claim 16, Column 34, Line 24, delete "sRNA" and insert --siRNA--

Claim 16, Column 34, Line 26, delete "sRNA" and insert --siRNA--

Signed and Sealed this
Thirtieth Day of April, 2024

Katherine Kelly Vidal
*Director of the United States Patent and Trademark Office*

SEQUENCE LISTING

```
<160> NUMBER OF SEQ ID NOS: 15

<210> SEQ ID NO 1
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: siRNA

<400> SEQUENCE: 1
ugacugagug gcugaguua                                                 19

<210> SEQ ID NO 2
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: siRNA

<400> SEQUENCE: 2
gaccuagccc agcugauaa                                                 19

<210> SEQ ID NO 3
<211> LENGTH: 19
<212> TYPE: RNA
```

```
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: siRNA

<400> SEQUENCE: 3
gaauggauuu gacgugaac                                                19

<210> SEQ ID NO 4
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: siRNA

<400> SEQUENCE: 4
gccgagaccu cuaaacuua                                                19

<210> SEQ ID NO 5
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: siRNA

<400> SEQUENCE: 5
ugagaugcuu ggacgaaaa                                                19

<210> SEQ ID NO 6
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: siRNA

<400> SEQUENCE: 6
gaaucagagg caaagugga                                                19

<210> SEQ ID NO 7
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: siRNA

<400> SEQUENCE: 7
ucucaguucu cuucacuca                                                19

<210> SEQ ID NO 8
<211> LENGTH: 8
<212> TYPE: PRT
<213> ORGANISM: Homo sapiens

<400> SEQUENCE: 8
```

-continued

Cys Pro Asn Lys Glu Lys Glu Cys
1               5

<210> SEQ ID NO 9
<211> LENGTH: 37
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: siRNA

<400> SEQUENCE: 9
uagcgacuaa acacaucaau aggcuaugaa gagauac                                37

<210> SEQ ID NO 10
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: siRNA

<400> SEQUENCE: 10
auguauuggc cuguauuag                                                    19

<210> SEQ ID NO 11
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: siRNA

<400> SEQUENCE: 11
augaacguga auugcucaa                                                    19

<210> SEQ ID NO 12
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: siRNA

<400> SEQUENCE: 12
ugguuuacau gucgacuaa                                                    19

<210> SEQ ID NO 13
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Peptide fragment based on WIP

<400> SEQUENCE: 13

Met Gly Ser Ser His His His His His His Ser Gly Gln Asp Ser Pro
1               5                   10                  15

```
Cys Glu Asp Glu Trp Glu Ser Arg Phe Tyr Phe His Pro Ile Ser Asp
            20                  25                  30

Leu Pro Pro Pro Glu Pro Tyr Val Gln Thr Thr Lys Ser Tyr Pro Ser
        35                  40                  45

Lys Leu Ala Arg Asn Glu Ser Arg Ser Gly Ser Asn Pro Arg Glu
    50                  55                  60

<210> SEQ ID NO 14
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Peptide fragment based on WIP

<400> SEQUENCE: 14

Asp Leu Pro Pro Pro Glu Pro Tyr Val Gln Thr Thr Lys Ser Tyr Pro
1               5                   10                  15

Ser Lys Leu Ala Arg
            20

<210> SEQ ID NO 15
<211> LENGTH: 56
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Peptide fragment based on WIP

<400> SEQUENCE: 15

Met Gly Ser Ser His His His His His His Ser Gly Gln Asp Ser Pro
1               5                   10                  15

Cys Glu Asp Glu Trp Glu Ser Arg Phe Tyr Phe His Pro Ile Ser Asp
            20                  25                  30

Leu Pro Pro Pro Glu Pro Tyr Val Gln Thr Thr Lys Ser Tyr Pro Ser
        35                  40                  45

Lys Leu Ala Arg Asn Glu Ser Arg
    50                  55
```